United States Patent [19]

Chupp et al.

[11] Patent Number: 4,618,713

[45] Date of Patent: Oct. 21, 1986

[54] PREPARATION OF 2'-METHYL-2-HALOACETANILIDES

[75] Inventors: John P. Chupp, Kirkwood; Michael J. Miller, Manchester, both of Mo.

[73] Assignee: Monsanto Company, St. Louis, Mo.

[21] Appl. No.: 530,154

[22] Filed: Sep. 7, 1983

[51] Int. Cl.$^4$ .................. C07C 102/00; C07C 103/34; C07C 149/42

[52] U.S. Cl. ................................. 564/214; 564/142; 564/412; 564/440

[58] Field of Search .................. 564/214, 412, 440

[56] References Cited

U.S. PATENT DOCUMENTS

| | | | |
|---|---|---|---|
| 3,162,681 | 12/1964 | Connors et al. | 564/442 X |
| 3,983,174 | 9/1976 | Richter et al. | 564/442 X |
| 4,172,095 | 10/1979 | Steinman et al. | 564/442 X |
| 4,282,380 | 8/1981 | Lutz | 564/398 |
| 4,496,765 | 1/1985 | Ka et al. | 564/440 |

OTHER PUBLICATIONS

Wagner et al., "Synthetic Organic Chemistry", p. 8 (1963).

*Primary Examiner*—Robert V. Hines
*Attorney, Agent, or Firm*—Robert B. Martin

[57] ABSTRACT

This invention relates to a process for preparing 2'-methyl-2-haloacetanilides by selective catalytic hydrogenation of 2'-(halomethyl)-2-haloacetanilides. The 2'-(halomethyl)-2-haloacetanilides are initially prepared by reacting an ortho-(halomethyl) aniline or its anilinium salt with a haloacetyl halide.

13 Claims, No Drawings

PREPARATION OF 2'-METHYL-2-HALOACETANILIDES

BACKGROUND OF THE INVENTION

1. Field of the Invention

This invention relates to a process for preparing 2'-methyl-2-haloacetanilides from ortho-(halomethyl) anilines and their anilinium salts by reaction with haloacetyl halides and subsequent catalytic reaction with hydrogen.

2. Description of the Prior Art

2-Haloacetanilide herbicides are known in the prior art and have been produced by haloacetylation of the appropriate amine generally in the presence of caustic soda to neutralize by-product hydrogen halide.

For example, in Hamm, et al., U.S. Pat. No. 2,863,752, a specific class of tertiary-2-haloacetanilide herbicides is prepared by gradually adding an acid chloride of a 2-haloacetic acid, e.g., chloroacetyl chloride, to excess N-substituted aniline. The secondary aniline is preferably dissolved in a suitable solvent, e.g., ethylene dichloride, mixed with aqueous sodium hydroxide and refrigerated. The reaction is conducted under refrigerated conditions to prevent an excessive rate of reaction. After the reaction, the recovered organic phase is successively washed with dilute acid, dilute base and water. The product 2-haloacetanilide is then recovered from the organic solvent by vacuum evacuation.

A similar process is described in Vogel, et al., U.S. Pat. No. 3,937,730 wherein a secondary aniline is reacted with an anhydride or acid halide of chloroacetic acid in the presence of a base; e.g., triethylamine.

In U.K. Patent Application No. GB 2,070,584 A, a secondary aniline is slowly added to a solution of an acid chloride (e.g. chloroacetyl chloride and methoxyacetyl chloride) in an inert solvent. The aniline is added at 20°–80° C. over the course of 0.5 to 1.5 hours. After subsequent evacuation in the same temperature range, to a pressure of 300–400 mm Hg, base neutralization, recovery of the organic phase and evaporative removal of the solvent, the product tertiary acetamide is recovered in the form of a melt.

None of these references describe a procedure for producing secondary 2-haloacetanilides from an ortho-(halomethyl) aniline or its anilinium salt.

Secondary haloacetanilides are useful as precursors for the production of N-(hydrocarbyloxymethyl)-2-haloacetanilide herbicides, particularly N-(ethoxymethyl)-2'-methyl-6'-(trifluoromethyl)-2-chloroacetanilide.

It is an object of the present invention to provide a new process for producing secondary 2-haloacetanilides.

It is another object of this invention to provide a process for producing secondary 2-haloacetanilides from an ortho-(halomethyl) aniline or its anilinium salt.

It is a further object of this invention to provide a method for producing secondary 2-haloacetanilides, preferably 2'-methyl-2-chloroacetanilides, which are useful for the preparation of specific aniline-derived herbicide compounds.

Other objects and advantages will become apparent from the following disclosure.

SUMMARY OF THE INVENTION

This invention broadly pertains to a process for preparing 2'-methyl-2-haloacetanilides wherein an ortho-(halomethyl) aniline or its anilinium salt is reacted in a refluxing solvent with a haloacetyl halide to produce a 2'-(halomethyl)-2-haloacetanilide which is thereafter reductively dehalogenated by catalytic reaction with hydrogen to selectively yield the desired 2'-methyl-2-haloacetanilide. More particularly, the present invention describes an improved process for preparing 2'-methyl-2-chloroacetanilides from ortho-(chloromethyl) anilines or their anilinium salts by sequential chloroacetylation and selective hydrodehalogenation.

DETAILED DESCRIPTION OF THE INVENTION

This invention pertains to a process for preparing 2'-methyl-2-haloacetanilides from an ortho-(halomethyl) aniline or its anilinium salt. The ortho-(halomethyl) aniline or its anilinium salt preferably has one or more of a variety of nuclear substituents on the aniline ring including alkyl, alkoxy, alkoxyalkyl, haloalkyl, halogen, alkenyl, alkenyloxy, alkynyl, alkynyloxy, aryl, aryloxy, aralkyl or aralkyloxy, as desired in the ultimate product. For example, particularly desirable substituents on the aniline ring positioned ortho to the aniline nitrogen include trifluoromethyl, methoxy, ethyl and isobutoxy. Generally, the selection of nuclear substituents is made to introduce desired herbicidal properties into the product, or in materials that can be prepared using the product, while avoiding substituents that interact with solvents or reactants employed in a manner inconsistent with the overall objects of processes described herein.

The ortho-(halomethyl) aniline or its anilinium salt starting material is conveniently prepared from ortho-(methylthiomethyl) anilines, optionally having desired nuclear substituents, by their initial conversion to the corresponding sulfoxide followed by reaction of the sulfoxide with hydrogen halide in an appropriate solvent to yield a solution that contains the corresponding ortho-(halomethyl) aniline. For example, the sulfoxide of the corresponding ortho-(methylthiomethyl) aniline is preferably reacted with hydrogen chloride to yield an ortho-(chloromethyl) aniline. An ortho-(chloromethyl) anilinium salt can then be precipitated from this solution. Ortho-(methylthiomethyl) anilines have been produced by sulfilimine rearrangement from corresponding nuclear substituted anilines. A typical sulfilimine rearrangement proceeds as follows: an appropriately nuclear substituted aniline is reacted with dimethyl sulfide in the presence of base and an oxidizing agent such as N-chlorosuccinimide or tert-butyl hypochlorite to give an aromatic sulfilimine product having a —N=S(CH$_3$)$_2$ group. The sulfilimine rearranges upon heating or catalysis to provide ortho-(methylthiomethyl) anilines. Commonly assigned, copending U.S. Pat. No. 4,496,765 entitled "Preparation of 2-(Methylthiomethyl)-6-(Trifluoromethyl) Aniline from Ortho-Aminobenzotrifluoride" filed on an even date herewith in the names of Chupp, Balthazor and Ku, and incorporated herein by reference, for example, describes a particularly preferred procedure for producing 2-(methylthiomethyl)-6-(trifluoromethyl) aniline from ortho-aminobenzotrifluoride. The intermediate sulfoxide is then prepared by oxidation of the ortho-(methylthiomethyl) aniline, for example, by reaction with hydrogen peroxide. The resulting ortho-(methylsulfinylmethyl) aniline is thereafter reacted with an acid halide, for example hydrogen chloride, producing a solution that contains free ortho-(chloromethyl) aniline. This reaction is generally carried out in an appropriate solvent; e.g., ethylene dichloride.

The anilinium salt can be recovered by treating the sulfoxide-acid halide reaction product solution with an appropriate acid, preferably hydrogen chloride and stirring. The solution is preferably cooled to about 0° to 5° C. during the hydrogen chloride treatment. Precipitation and filtration of the anilinium salt results in salt yields of up to about 95% or more.

In an alternative procedure, certain ortho-(methylthiomethyl) anilines can be reacted under anhydrous conditions with a halogenating agent, preferably such as chlorine or sulfuryl chloride, to produce a cyclic sulfilimine hydrochloride salt which, upon the addition of stoichiometric amounts of water, hydrolyzes to the sulfoxide and hydrogen chloride. The sulfoxide and hydrogen halide formed in situ react, as described above, to produce a ortho-(chloromethyl) aniline in a single vessel, without having to separately isolate the sulfoxide. Excess water is removed by azeotropic distillation. If desired, the anilinium salt can then be recovered as noted above. Additional details concerning various steps in the preparation of the anilinium salt from a nuclear substituted aniline, as briefly outlined above, can also be found in commonly assigned, copending application Ser. No. 358,772 entitled "Manufacture of Ortho-Methyl Anilines From Ortho-Amino Benzyl Sulfoxides" filed on Mar. 17, 1982 in the names of J. P. Chupp, et al., incorporated herein by reference.

Precipitation of the ortho-(chloromethyl) aniline as its corresponding anilinium salt is preferably effected in such a manner as to ensure that substantially all sulfur-containing impurities are separated from the anilinium salt. This is important since sulfur impurities represent a potential poison for the hydrogenation catalysts used in the subsequent selective hydrogenation step of this invention. A substantial sulfur-free anilinium salt can be obtained by selecting a solvent that has a limited capability for dissolving the anilinium salt but a high capacity for retaining the sulfur compounds in solution. Ethylene dichloride is a suitable solvent; other appropriate solvents can readily be determined employing simple solubility tests.

In accordance with a preferred embodiment of the present invention, an ortho-(chloromethyl) anilinium salt is reacted with chloroacetyl chloride to yield a 2'-(chloromethyl)-2-chloroacetanilide. This reaction is conducted in a substantially inert solvent at reflux. The solvent should be substantially inert to both the reactants and the products formed. Included in the class of suitable solvents are aliphatic and aromatic hydrocarbons, chlorinated hydrocarbons, ethers and esters. Preferred solvents include ethylene dichloride and toluene. The 2'-(chloromethyl)-2-chloroacetanilide product is generally recovered as a solid by evaporating the solvent from the reaction system.

The anilinium salt is added to the solvent and chloroacetyl chloride is then combined with this mixture. The combination can be accomplished conveniently by adding the chloroacetyl chloride to the anilinium salt-solvent mixture. A slight mol excess (e.g., 1.05–1.5 equivalents) of the chloroacetyl chloride is preferably used to ensure complete conversion. Larger amounts of chloroacetyl chloride are preferably avoided since any excess is preferably removed from the reaction mixture before further processing. Excess chloroacetyl chloride can be removed from the reaction mixture by treatment with aqueous sodium carbonate.

The chloroacetylation reaction is conducted using a suitable refluxing solvent so as to promote the thermal dissociation of the anilinium chloride salt to free ortho-(chloromethyl) aniline therein. For convenience, the reaction is generally conducted under atmospheric reflux conditions, although other pressures can be used. Dissociation of the anilinium salt must occur before the desired chloroacetylation reaction proceeds to completion. Reflux conditions are preferably established at a temperature above about 50° C. so as to suitably promote the necessary thermal dissociation. In this case, the dissociation reaction is accompanied by gaseous hydrogen chloride liberation. The chloroacetyl chloride then reacts with the free aniline to form the desired 2-chloroacetanilide product, liberating additional gaseous hydrogen chloride. Reflux conditions are preferably continued until hydrogen chloride evolution ceases, generally for about 0.5 to about 1.5 hours.

In an alternate procedure, the 2'-(chloromethyl)-2-chloroacetanilide is produced directly from the solution containing the 2-(chloromethyl) aniline without separately recovering, i.e., isolating, the anilinium salt. This procedure is particularly advantageous because it can be conducted in "one-pot." As noted above, after treating the sulfoxide with hydrogen chloride or the ortho-(methylthiomethyl) aniline with chlorine, then water and subsequent azeotropic removal of excess water, the solution contains free ortho-(chloromethyl) aniline and/or its salt. Direct treatment of this solution with chloroacetyl chloride produces the desired 2'-(chloromethyl)-2-chloroacetanilide product. Since the 2-chloroacetanilide product is generally recovered as a solid by subsequent solvent evaporation, the product obtained in this manner may often contain low valent sulfur impurities. As noted above, failure to remove the sulfur compounds from the product may result in decreased efficiency in the subsequent hydrogenation step because the preferred hydrogenation catalysts are generally susceptible to sulfur poisoning. In this embodiment, these sulfur impurities are preferably removed by treatment of the solid chloroacetanilide or solutions thereof with base solutions such as aqueous sodium carbonate and an oxidizing agent such as aqueous sodium hypochlorite or hydrogen peroxide.

In the second step of the process for producing the desired 2'-methyl-2-chloracetanilide, the 2'-(chloromethyl)-2-chloroacetanilide is selectively hydrodehalogenated. First, the 2'-(chloromethyl)-2-chloroacetanilide is dissolved/suspended in an appropriate solvent together with a suitable catalyst; e.g., palladium-doped activated carbon (Pd/C), and an appropriate hydrogen halide scavenger. Polar solvents such as lower alcohols, water, esters, e.g. ethyl acetate and ethers are generally preferred. Methanol and ethanol, optionally aqueous, are particularly preferred. The scavenger can be selected from a wide variety of organic and inorganic bases. Typical scavengers include triethylamine, trimethylamine, ammonia, sodium acetate, pyridine or diisopropylethylamine. Triethylamine is a particularly preferred scavenger. The scavenger neutralizes hydrogen halide as it is formed, and solvent-soluble scavengers are preferred.

In order to maximize selective hydrogenation, only about one equivalent or a slight molar excess of base (i.e., acid scavenger) should preferably be used. For example, only about 1.0 to about 1.1 mols of acid scavenger per mol of 2-chloroacetanilide are preferably used. If a larger quantity of scavenger is used, there is a greater likelihood of overreduction. When ammonia is used as a scavenger, it is often difficult to stop the selective hydrogenation at the chloroacetyl stage. Consequently, careful control of the amount of ammonia added may be necessary to obtain the desired product.

Palladium is the preferred hydrogenation catalyst, although other known hydrogenation netal catalysts, including platinum, rhodium, nickel and the like, can also be used. The catalyst is preferably deposited on a porous support. The catalyst is generally present in amounts less than 10% by weight of the reaction mixture.

The hydrogenation temperature may range from about 10° C. to 100° C., preferably from 20° C. to about 40° C., and pressure may range from about 0 to 800 psig. For maximum selectivity low pressures, i.e., below about 100 psig, are particularly preferred. The reaction mixture is typically agitated in the presence of an atmosphere of pressurized hydrogen to produce the desired 2'-methyl-2-chloroacetanilide. The reductive hydrogenation is preferably stopped when the hydrogen uptake, as measured, for example, by a decreasing reactor pressure, essentially ceases. Generally, only about 0.5–1.5% of overreduction occurs. Longer reaction times, higher reaction temperatures and higher reaction pressures all lead to a reduction in selectivity.

Because of the known lability of the 2-halogen on the N-acetyl radical, it is unexpected that the halogen moiety of the haloalkyl aromatic substituent can be preferentially replaced using catalytic hydrogenation, while preserving the halogen at the 2-acetyl position. Moreover, it has been discovered that by conducting the hydrogenation reaction under the preferred conditions exemplified herein, it is possible to substantially avoid this unwanted side-dehalogenation which otherwise occurs.

The following examples are included for illustrative purposes only and are not intended to limit the scope of the invention.

EXAMPLE 1

This example demonstrates a method for preparing an anilinium salt, specifically 2-(chloromethyl)-6-(trifluoromethyl) anilinium chloride from a sulfoxide.

A solution of 20.0 grams (0.0844 mol) of 2-(methylsulfinylmethyl)-6-(trifluoromethyl) aniline in 250 ml of ethylene dichloride in a 500 ml round bottom flask equipped with an efficient stirrer, an HCl inlet tube, distilling head and thermometer was treated at room temperature with gaseous HCl until the initial tacky precipitate gave way to a cloudy mixture (3–5 minutes). The mixture was then heated rapidly to 60°–63° C. while HCl was bubbled through the mixture. After 10 minutes of heating and HCl treatment, 1 ml of $H_2O$ was added, and heating and HCl treatment were continued until the mixture became clear (generally 10–15 minutes after $H_2O$ addition) (often a very small amount of insoluble material will be observed on the sides of the flask at this point). The clear orangish solution was then further heated (the HCl was stopped at this point) and solvent and $H_2O$ were distilled off until no $H_2O$ remained in the reaction flask (typically 50–60 ml of solvent were removed over 15–20 minutes). This mixture contains free 2-(chloromethyl)-6-(trifluoromethyl) aniline and constitutes the precursor for the anilinium chloride salt. The clear yellow solution was then cooled, with stirring and HCl bubbling through to 0° to 5° C. The precipitated solid was collected by filtration and washed with 50 ml of cold ethylene dichloride, then sucked as dry as possible. Yield of off-white 2-(chloromethyl)-6-(trifluoromethyl) anilinium chloride was typically 95% (contained a small amount of water). Analysis calculated for $C_8H_8Cl_2F_3N$: C, 39.05; H, 3.28; N, 5.69; Found: C, 41.36; H, 3.43; N, 5.98.

EXAMPLE 2

This example demonstrates an alternative method for preparing an anilinium chloride starting material, specifically 2-(chloromethyl)-6-(trifluoromethyl) anilinium chloride.

Chlorine (76.0 grams, 1.07 mol) was bubbled into a mechanically stirred solution of 221.0 grams (1.00 mol) of 2-(methylthiomethyl)-6-(trifluoromethyl) aniline in 2 liters of ethylene dichloride over 60 minutes while maintaining the reaction temperature below 20° C. The mixture was then heated to 60° C. while maintaining a steady stream of HCl bubbling through. Water (25 ml, 1.4 mol) was added and the HCl treatment was maintained at 60° C. for 15 minutes at which point a clear solution was obtained. Excess water was removed by azeotropic distillation (780 ml of solvent were removed) and the resulting solution was cooled to 0° C. with a steady stream of HCl bubbling through to precipitate the anilinium chloride salt. Filtration, washing of the solids with 150 ml. of cold ethylene dichloride and air-drying gave 228.0 grams (92.7%) of off-white 2-(chloromethyl)-6-(trifluoromethyl) anilinium chloride.

EXAMPLE 3

In a preferred variation on the procedure of Example 2, HCl was not introduced into the reaction mixture until time for precipitation of the anilinium salt. Chlorine (6 grams, 0.084 mol) was passed into a solution of 17.5 grams (0.0792 mol) of 2-(methylthiomethyl)-6-(trifluoromethyl) aniline in 160 ml of ethylene dichloride at 15°–21° C. Water (2 ml, 0.11 mol) was added and the mixture was then heated to 60°–65° C. After 30 minutes a clear solution was obtained. Excess water was removed by azeotropic distillation (65 ml of solvent were removed) and the solution was cooled to 0° C. with a stream of HCl bubbling through. The resulting solid anilinium salt was isolated by filtration yielding 17.7 grams (90.9%).

EXAMPLE 4

This example demonstrates a method for preparing 2'-(chloromethyl)-6'-(trifluoromethyl)-2-chloracetanilide in toluene. Chloroacetyl chloride (3.6 g, 0.032 mol) was slowly added to 2-(chloromethyl)-6-(trifluoromethyl) anilinium chloride (7.8 g, 0.032 mol) and the mixture was heated at reflux for 40 minutes in 100 ml of toluene. The solvent was then evaporated and the solid residue (approx. quantitative crude yield) was recrystallized from methylcyclohexane containing a few percent ethyl acetate. The first batch of recovered product weighed 3.5 g; mp 101–101.5. Analysis calculated for $C_{10}H_8Cl_2F_3NO$: C, 41.98; H, 2.82; N, 4.90; Found: C, 42.33; H, 2.79; N, 4.90.

EXAMPLE 5

This example and example 6 describe a method for preparing 2'-(chloromethyl)-6'-(trifluoromethyl)-2-chloroacetanilide in ethylene dichloride. Chloroacetyl chloride (CAC) (11 g, 0.097 mol) was slowly added to a slurry of 19.0 g (0.0772 mol) of 2-(chloromethyl)-6-(trifluoromethyl) anilinium chloride in 120 ml of ethylene dichloride and the mixture was heated to reflux. After 30 minutes at reflux (the mixture turned to a clear solution after 10 minutes), an additional 1.1 g (0.0097 mol) of CAC was added and reflux was continued for 35 minutes (total reflux of 65 minutes). The solution was cooled to room temperature, washed with 80 ml of 10% aqueous sodium carbonate and dried using sodium sulfate. The solvent was removed in vacuo providing 20.73 g of off-white solid having an assay of 92% for an overall yield of 86.5%.

EXAMPLE 6

A slurry of 19.85 g (0.0947 mol) of 2-(chloromethyl)-6-(trifluoromethyl) anilinium chloride (prepared as in Example 1 from 20.0 g of sulfoxide) was refluxed in ethylene dichloride with 11.2 g (0.0991 mol) of chloroacetyl chloride for 30 minutes followed by addition of 1.0 g (0.0089 mol) of additional CAC and further reflux for 30 minutes. The virtually clear solution was then cooled to room temperature, washed with 10% aqueous sodium carbonate (80 ml) and dried using sodium sulfate. Evaporation and drying gave 22.14 g of white 2'-(chloromethyl)-6'-(trifluoromethyl)-2-chloroacetanilide assaying 93.5% for an overall yield from sulfoxide of 85.7%.

EXAMPLE 7

This example describes a "one-pot" preparation of 2'-(chloromethyl)-6'-(trifluoromethyl)-2-chloroacetanilide from 2-(methylsulfinylmethyl)-6-(trifluoromethyl) aniline. A solution of 20.0 g (0.0844 mol) of sulfoxide in 250 ml of ethylene dichloride was treated with HCl and water as in Example 1. At the end of the 60°–63° C. heating period, 100 ml of solvent (and water) was removed by distillation. The resulting slightly yellow solution of 2-(chloromethyl)-6-(trifluoromethyl) aniline (i.e., anilinium chloride salt precursor) was cooled to 70°–75° C. and 12.1 g (0.107 mol) of chloroacetyl chloride was slowly added. The mixture was heated at reflux for 50 minutes, cooled to room temperature and stirred for 35 minutes with 100 ml of cold 10% aqueous sodium carbonate. The aqueous phase was discarded and the recovered organic phase was stirred for 30 minutes with an additional 100 ml of 10% aqueous sodium carbonate. The organic phase was evaporated to give 25.15 g of crude solid which was dissolved in 55 ml of methanol at 55° C. and precipitated by water addition. The solid was filtered, washed with two portions of cold 2:1 water:methanol (75 ml total), 25 ml of dilute aqueous sodium hypochlorite solution and finally two 50 ml portions of water. The resulting off-white solid after drying weighed 21.56 g and assayed 90.2% by weight of 2'-(chloromethyl)-6'-(trifluoromethyl)-2-chloroacetanilide for an overall yield of 80.5%.

EXAMPLE 8

This example describes a "one-pot" preparation of 2'-(chloromethyl)-6'-(trifluoromethyl)-2-chloroacetanilide from 2-(methylthiomethyl)-6-(trifluoromethyl) aniline. A solution of 20.01 g (0.0905 mol) of 2-(methylthiomethyl)-6-(trifluoromethyl) aniline in 160 ml of ethylene dichloride was treated with chlorine gas, then HCl and water as described in Example 2. After completion of the heating period and distillation of 80 ml of solvent and water, the solution of 2-(chloromethyl)-6-(trifluoromethyl) aniline was cooled to 70° C., 12.1 g (0.107 mol) of chloroacetyl chloride was slowly added and the mixture was refluxed for 40 minutes. After an additional 0.97 g (0.0086 mol) of chloroacetyl chloride and 20 minutes of additional reflux, the mixture was cooled to 20° C., then stirred with 100 ml of 10% aqueous sodium carbonate. The organic phase was stirred for 40 minutes with 100 ml of additional 10% aqueous sodium carbonate then evaporated. The resulting crude solid was dissolved in methanol (55 ml) and water was added at 55° C. to reprecipitate the solid. This solid was filtered, washed with 100 ml of water, 30 ml of dilute aqueous sodium hypochlorite and 100 ml of water and air-dried to give 23.5 g of 2'-(chloromethyl)-6'-(trifluoromethyl)-2-chloroacetanilide having an assay of 89.2% for an overall yield of 81.0%.

Examples 9–12 describe various procedures for promoting the selective hydrogenation of 2'-(chloromethyl)-6'-(trifluoromethyl)-2-chloroacetanilide to produce 2'-methyl-6'-(trifluoromethyl)-2-chloroacetanilide.

EXAMPLE 9

A solution of 8.01 g (0.0262 mol based on 93.5% assay) of 2'-(chloromethyl)-6'-(trifluoromethyl)-2-chloroacetanilide (prepared as in example 6) and 4.0 ml (0.029 mol) of triethylamine in 60 ml of ethanol was shaken with 0.160 g of 10% Pd/C under 20–50 psi of $H_2$ pressure at room temperature. When $H_2$ uptake was complete (4.0 hr.), the mixture was filtered to remove catalyst and partitioned between 100 ml of methylene chloride and 50 ml of water. The organic phase, combined with a small methylene chloride wash of the aqueous phase, was washed with two 50 ml portions of water and was dried using magnesium sulfate. Solvent removal in vacuo provided 6.92 g of white 2'-methyl-6'-(trifluoromethyl)-2-chloroacetanilide assaying 92.1% for a yield of 96.7%.

The product contained 1.12% of 2'-methyl-6'-(trifluoromethyl) acetanilide arising from removal of both chlorines in the starting material.

EXAMPLE 10

A solution of 12.01 g (0.0393 mol based on 93.5% assay) of 2'-(chloromethyl)-6'-(trifluoromethyl)-2-chloroacetanilide (prepared as in Example 6) and 6.0 ml (0.043 mol) of triethylamine in 60 ml of ethanol was shaken with 0.242 g of 10% Pd/C under 20–50 psi of $H_2$ pressure at room temperature. When $H_2$ uptake ceased (3.5 hr.), the mixture was filtered to remove catalyst (10–15 ml of ethanol were used as a wash) and 150 ml of water were added to the filtrate. The solution and precipitate were cooled in an ice bath for 30 minutes; the solid was then collected by filtration, washed with two 20 ml portions of cold water and air-dried. The yield of white 2'-methyl-6'-(trifluoromethyl)-2-chloroacetanilide was 9.18 g with assay 97.0% (yield of 90.1%) with 0.46% of overreduced product present.

EXAMPLE 11

A solution of 2.02 g (7.06 mmol) of 2'-(chloromethyl)-6'-(trifluoromethyl)-2-chloroacetanilide and 1.0 ml (7.2 mmol) of triethylamine in 60 ml of ethyl acetate was shaken with 79.8 mg of 10% Pd/C under an initial $H_2$ pressure of 50 psi. After 19 hr., the mixture was filtered and evaporated to give 1.57 g of 2'-methyl-6'-(trifluoromethyl)-2-chloroacetanilide assaying 94.2% (yield 83.3%) and contaminated with 1.3% of overreduced product.

EXAMPLE 12

A solution of 8.00 g (0.028 mol) of 2'-(chloromethyl)-6'-(trifluoromethyl)-2-chloroacetanilide and 1.86 g (0.032 mol) of 29% aqueous ammonia in 60 ml of ethanol was shaken with 0.165 g of 10% Pd/C under an initial $H_2$ pressure of 50 psi. After 2.0 hr., the mixture was filtered to remove catalyst and ammonium chloride. Gas chromatographic analysis indicated approximately 4.1% overreduction.

Although preferred embodiments of this invention have been discussed herein, those skilled in the art will appreciate that changes and modifications may be made without departing from the spirit and the scope of this invention, as defined in and limited only by the scope of the appended claims. For example, while certain aspects of the present invention have been described solely with reference to a preferred embodiment involving the reaction between ortho-(chloromethyl) anilines or their anilinium salts and chloroacetyl chloride, and the reaction products thereof, the invention is believed to be more broadly applicable to various other ortho-(halomethyl) anilines or their anilinium salts as well as other haloacetyl halides.

We claim:

1. A process for preparing a 2'-methyl-2-haloacetanilide which comprises reacting a 2'-(halomethyl)-2-haloacetanilide with hydrogen in the presence of an acid scavenger and hydrogenation catalyst, whereby said 2'-(halomethyl)-2-haloacetanilide is selectively hydrogenated to 2'-methyl-2-haloacetanilide.

2. A process for preparing a 2'-methyl-2-haloacetanilide comprising:
   (a) reacting an ortho-(halomethyl) aniline or its anilinium salt with a haloacetyl halide in the presence of an inert solvent to produce a 2'-(halomethyl)-2-haloacetanilide; and
   (b) thereafter reacting the 2'-(halomethyl)-2-haloacetanilide with hydrogen in the presence of an acid scavenger and hydrogenation catalyst, whereby said 2'-(halomethyl)-2-haloacetanilide is selectively hydrogenated to a 2'-methyl-2-haloacetanilide.

3. The process of claim 1 wherein said 2'-halomethyl)-2-haloacetanilide is a 2'-(chloromethyl)-2-chloroacetanilide.

4. The process of claim 2 wherein said ortho-(halomethyl) aniline is an ortho-(chloromethyl) aniline and said haloacetyl halide is chloroacetyl chloride.

5. The process of claim 2 wherein an excess of chloroacetyl chloride is reacted with said ortho-(chloromethyl) aniline or its anilinium salt.

6. The process of claim 1 wherein about 1.0 to about 1.1 mols of said acid scavenger per mol of said 2'-(halomethyl)-2-haloacetanilide are used.

7. The process of claim 1 wherein the reaction of said 2'-(halomethyl)-2-haloacetanilide with hydrogen is terminated when the hydrogen uptake essentially ceases.

8. The process of claim 3 wherein the ortho-(chloromethyl) aniline or its anilinium salt has a trifluoromethyl group substituted on the aniline ring ortho to the aniline nitrogen.

9. The process of claim 8 wherein the ortho-(chloromethyl) aniline or its anilinium salt additionally has a chlorine substituted on the aniline ring para to the aniline nitrogen.

10. The process of claim 3 wherein the ortho-(chloromethyl) aniline or its anilinium salt has a methoxy group substituted on the aniline ring ortho to the aniline nitrogen.

11. The process of claim 3 wherein the ortho-(chloromethyl) aniline or its anilinium salt has an ethyl group substituted on the aniline ring ortho to the aniline nitrogen.

12. The process of claim 3 wherein the ortho-(chloromethyl) aniline or its anilinium salt has an isobutoxy group substituted on the aniline ring ortho to the aniline nitrogen.

13. The process of claim 1 wherein the acid scavenger is selected from the group of bases consisting of triethylamine, trimethylamine, ammonia, sodium acetate, pyridine or diisopropylethylamine.

* * * * *